(12) United States Patent
Nakanishi et al.

(10) Patent No.: US 9,975,851 B2
(45) Date of Patent: *May 22, 2018

(54) METHOD FOR PRODUCING 2-ACYLIMINOPYRIDINE DERIVATIVE

(71) Applicant: MEIJI SEIKA PHARMA CO., LTD., Tokyo (JP)

(72) Inventors: Nozomu Nakanishi, Yokohama (JP); Shigeki Kitsuda, Yokohama (JP); Yoshimasa Fukuda, Yokohama (JP)

(73) Assignee: MEIJI SEIKA PHARMA CO., LTD., Chuo-ku, Tokyo (JP)

( * ) Notice: Subject to any disclaimer, the term of this patent is extended or adjusted under 35 U.S.C. 154(b) by 5 days.

This patent is subject to a terminal disclaimer.

(21) Appl. No.: 15/122,977

(22) PCT Filed: Mar. 4, 2015

(86) PCT No.: PCT/JP2015/056409
§ 371 (c)(1),
(2) Date: Sep. 1, 2016

(87) PCT Pub. No.: WO2015/137216
PCT Pub. Date: Sep. 17, 2015

(65) Prior Publication Data
US 2017/0073312 A1 Mar. 16, 2017

(30) Foreign Application Priority Data

Mar. 10, 2014 (JP) .................................. 2014-046202

(51) Int. Cl.
*C07D 213/75* (2006.01)
(52) U.S. Cl.
CPC .................................. *C07D 213/75* (2013.01)
(58) Field of Classification Search
CPC .................................................... C07D 213/75
USPC ........................................................ 546/265
See application file for complete search history.

(56) References Cited

U.S. PATENT DOCUMENTS 9,357,776 B2 * 6/2016 Nakanishi .............. A01N 43/78
2014/0213791 A1 * 7/2014 Nakanishi .............. A01N 43/78
546/265

FOREIGN PATENT DOCUMENTS

| EP | 0268915 A2 | 6/1988 |
| EP | 0432600 A2 | 6/1991 |
| EP | 0639569 A1 | 2/1995 |
| JP | 578323 A | 3/1993 |
| JP | 2009292799 A | 12/2009 |
| WO | 2012029672 A1 | 3/2012 |
| WO | 2013031671 A1 | 3/2013 |

OTHER PUBLICATIONS

Botho Kickhofen et al; "Fritz Kröhnke und Botho Kickhöfen: Synthesen von Imidazo-pyridinen, II," Chemische Berichte , 1955, vol. 88, pp. 1103 to 1108.
International Preliminary Report on Patentability and Written Opinion of the International Searching Authority issued from the International Bureau in counterpart International Application No. PCT/JP2015/056409, dated Sep. 22, 2016.
Masaya Matsumura et al ;"Species-specific insecticide resistance to imidacloprid and fipronil in the rice planthoppers Nilaparvata lugens and Sogatella furcifera in East and South-east Asia," Pest Management Science 2008, vol. 64 No. 11, pp. 1115-1121 (7 pages total).
Botho Kickhofen et al; "Fritz Kröhnke and Botho Kickhöfen: Synthesen von Imidazo-pyridinen, II," Chemische Berichte, 1955, vol. 88, pp. 1103 to 1108.
Wladyslaw Peitrzycki et al; "Tautomerism and Rotamerism in 2-Methylamino-, 2-Anilino-, 2-Acetamido-, and 2-Benzamido-Pyridines" Bull. Soc. Chim. Belg. vol. 102 No. 11-12; pp. 709-717 (1993) (9 pages total).

(Continued)

*Primary Examiner* — Patricia L Morris
(74) *Attorney, Agent, or Firm* — Sughrue Mion, PLLC

(57) ABSTRACT

A method for producing a compound represented by formula (I) comprises the steps of:
acylating an amino group at position 2 of a compound represented by formula (A) by use of trifluoroacetic acid as an acylating agent to thereby produce a compound represented by formula (B); and
further alkylating a nitrogen atom at position 1 of the compound represented by formula (B), as follows

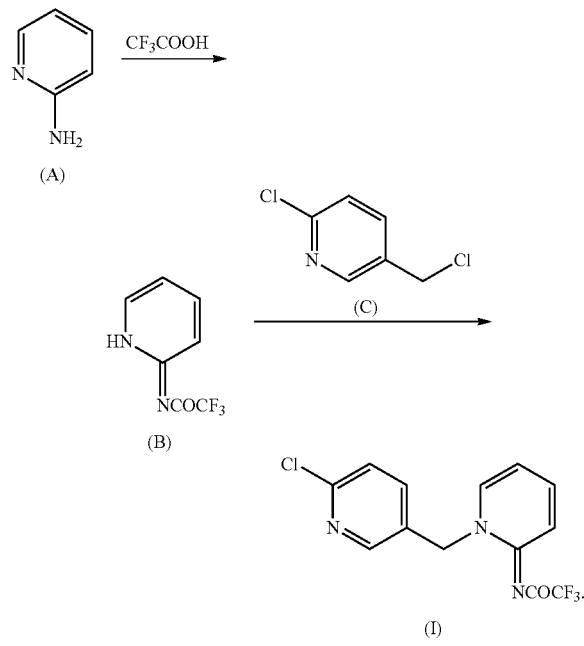

4 Claims, No Drawings

(56) References Cited

OTHER PUBLICATIONS

Shin-Jikken Kagaku Kouza, "Synthesis and reaction of organic compounds (II)," New Experimental Chemistry, vol. 14, p. 1107; Issued Dec. 20, 1977 (8 pages total).

* cited by examiner

METHOD FOR PRODUCING 2-ACYLIMINOPYRIDINE DERIVATIVE

CROSS REFERENCE TO RELATED APPLICATIONS

This application is a National Stage of International Application No. PCT/JP2015/056409 filed Mar. 4, 2015, claiming priority based on Japanese Patent Application No. 2014-046202 filed Mar. 10, 2014, the contents of all of which are incorporated herein by reference in their entirety.

TECHNICAL FIELD

The present invention relates to a method for producing a derivative having a 2-acyliminopyridine structure.

BACKGROUND ART

A 2-acyliminopyridine derivative represented by formula (I) described later is a compound useful as a pest control agent, as described in Patent Literature 5.

Methods described in Patent Literatures 1 to 5 and Non Patent Literature 2 are each known as a method for producing a pest control agent having a 2-acyl iminopyridine structure.

However, Patent Literatures 1, 2, and 3, and Non Patent Literature 2 fail to describe production in which a compound represented by formula (B) described later is used as an intermediate. Moreover, these literatures do not specifically describe the production of a compound represented by formula (I) described later. Further, Non Patent Literature 3 discloses N-(pyridin-2(1H)-ylidene]-acetamide as a tautomer of 2-acetamide pyridine, but fails to describe a specific method for producing the tautomer, or a method for producing a haloacyl derivative thereof.

On the other hand, Patent Literatures 4 and 5 disclose a specific method for producing a compound represented by formula (I). Nevertheless, although the use of an acid anhydride such as trifluoroacetic anhydride as an acylating agent generally results in a high yield in many cases because of the high reactivity, 1 equivalent of a carboxylic acid compound is by-produced. Hence, the use is industrially and economically disadvantageous and also has a great impact in the environmental aspect.

Meanwhile, the reactivity of carboxylic acid compounds is generally low, and it is difficult to use such carboxylic acid compounds for the acylation without any modification. Hence, a condensation agent is used in combination in many cases. Nevertheless, the combined use of a condensation agent brings about a problem that another waste product is generated. In other methods, an acid chloride of a carboxylic acid compound is often formed and used for the acylation. However, particularly as to trifluoroacetic acid, it is normally difficult to synthesize an acid chloride thereof unless a co-catalyst is added, as described in Non Patent Literature 4. Further, trifluoroacetyl chloride is a gas having a boiling point of −27° C., and a dedicated facility is required for the industrial use of an acid chloride derived from trifluoroacetic acid. Meanwhile, it is also possible to obtain an acylated product, as described in Patent Literature 6, by dehydrating under reflux trifluoroacetic acid together with a high-boiling-point solvent such as toluene or xylene. However, the reaction has to be carried out at a high temperature for a long period, which is industrially disadvantageous.

In sum, there has been no report so far that an acylated compound is obtained in a high yield using trifluoroacetic acid without using a condensation agent, without requiring a dedicated facility, and without needing a high-temperature, long-period reaction.

CITATION LIST

Patent Literature

[PTL 1] European Patent Application Publication No. 432600

[PTL 2] Japanese Unexamined Patent Application Publication No. Hei 05-78323

[PTL 3] European Patent Application Publication No. 268915

[PTL 4] International Publication No. WO2013/031671

[PTL 5] International Publication No. WO2012/029672

[PTL 6] Japanese Unexamined Patent Application Publication No. 2009-292799

Non Patent Literature

[NPL 1] Masaya Matsumura et al., Pest Management Science, 2008, Vol. 64, No. 11, pp. 1115 to 1121

[NPL 2] Botho Kickhofen et al., Chemische Berichte, 1955, Vol. 88, pp. 1103 to 1108

[NPL 3] Wladysl, aw Pietrzycki et al., Bulletin des Societes Chimiques Belges, 1993, Vol. 102, No. 11-12, pp. 709 to 717

[NPL 4] Shin-Jikken Kagaku Kouza (New Experimental Chemistry), Vol. 14, p. 1107

SUMMARY OF INVENTION

Technical Problem

An object of the present invention is to provide a production method for providing N-[1-((6-chloropyridin-3-yl)methyl)pyridin-2(1H)-ylide ne]-2,2,2-trifluoroacetamide represented by formula (I) described later in an amount required for a pest control agent stably, with low environmental load, and at a low cost.

Solution to Problem

According to a first aspect of the invention, the present inventors have found that, in a production method for obtaining a compound represented by the following formula (I) by using a compound represented by formula (A) as a starting substance, and a compound represented by formula (B) as an intermediate, the use of trifluoroacetic acid and a reaction reagent (X) makes it possible to produce a desired compound industrially and economically efficiently while consuming the reagent in a small amount and generating a small amount of waste product from the reaction. As a result, the present invention has been completed.

Specifically, the present invention provides the following method for producing a compound represented by formula (I) described below.

<1> Provided is a method for producing a compound represented by the following formula (I):

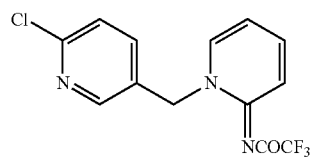

the production method comprising, as shown in the following reaction formula:

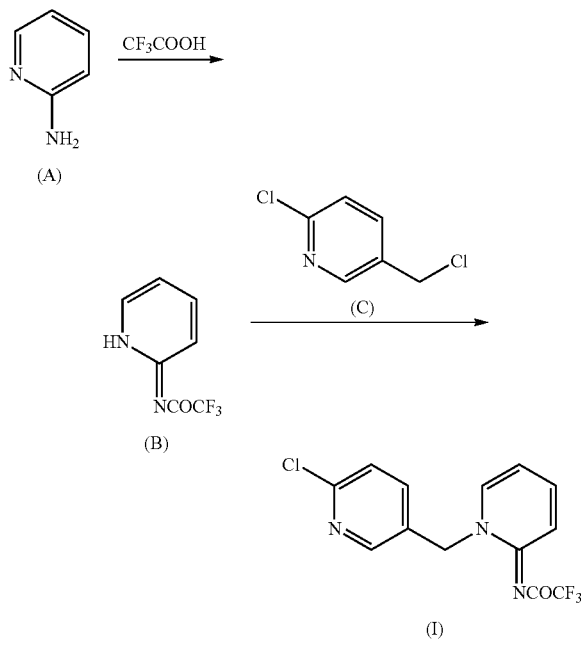

the steps of:
acylating an amino group at position 2 of a compound represented by formula (A) by use of trifluoroacetic acid and a reaction reagent (X) to thereby produce a compound represented by formula (B); and
further alkylating a nitrogen atom at position 1 of the compound represented by formula (B) by use of a compound represented by formula (C).
<2> The production method according to <1>, wherein the reagent (X) used simultaneously with the acylating agent is thionyl chloride.
<3> The production method according to <1> or <2>, wherein a base used in the reaction of the compound represented by formula (B) is pyridine or N-methylimidazole.
<4> The production method according to any one of <1> to <3>, wherein a solvent used in the reaction of the compound represented by formula (B) is an ether-based or ester-based solvent.
<5> The production method according to any one of <1> to <4>, wherein the trifluoroacetic acid as the acylating agent is used in an amount of 1.0 to 2.0 equivalents to the compound represented by formula (A), and simultaneously the thionyl chloride is used in an amount of 0.5 to 1.5 equivalents thereto, and the pyridine or N-methylimidazole is used in an amount of 1.5 to 3.0 equivalents thereto.

Herein, the base used for the production of the compound of formula (B) can be recovered and recycled, making it possible to reduce the generation of a waste product and the environmental load.

Advantageous Effects of Invention

According to the present invention, the compound represented by formula (I) useful as a pest control agent can be produced industrially and economically advantageously with low environmental load and, if necessary, in a one-pot manner.

DESCRIPTION OF EMBODIMENTS

The term "equivalent" of the base used herein is, for example, as follows: when 1 mol of potassium carbonate is used for 1 mol of a compound represented by formula (A), the potassium carbonate is 2 equivalents; when 1 mol of sodium hydroxide or sodium hydrogen carbonate is used therefor, the sodium hydroxide or sodium hydrogen carbonate is 1 equivalent; and when 1 mol of an organic base is used therefor, the organic base is 1 equivalent.

The "salt" used herein refers to an inorganic acid salt such as a hydrochloride, a sulfuric acid salt, or a nitric acid salt; an organic acid salt such as a trifluoroacetic acid salt, a difluoroacetic acid salt, or a dichloroacetic acid salt; or the like.

[Production Method]

The present invention will be described in further detail according to the following scheme.

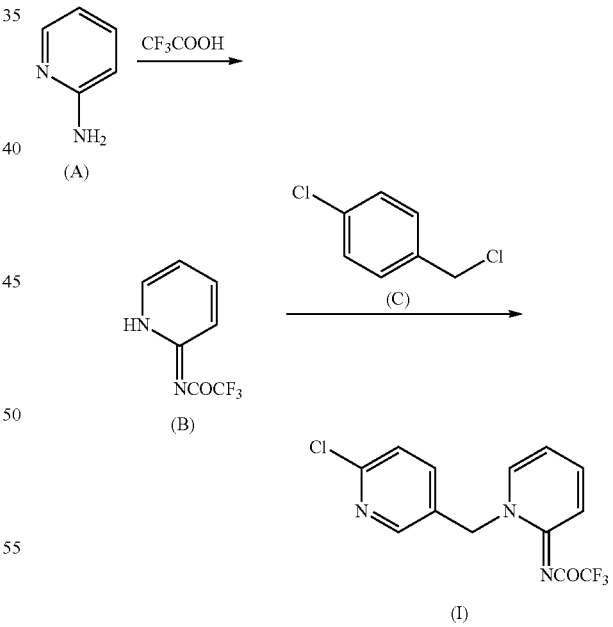

In addition, in the present invention, a compound represented by formula (B) shown in the above scheme may be used for the subsequent step, without post treatment or isolation.

[1] Production of Compound Represented by Formula (B) from Compound Represented by Formula (A)

A compound represented by formula (A) utilized may be a commercially available compound, or may be obtained by the method described in the literature (Journal of labeled compounds & radiopharmaceuticals (1987), 24(2), 119-123), for example.

A method for producing a compound represented by formula (B) from a compound represented by formula (A) by use of trifluoroacetic acid is as follows. Specifically, the method can be performed on the compound represented by formula (A) without a solvent or in a solvent which does not affect the reaction, in the presence of or in the absence of a base, and also by use of a reagent (X).

Here, the numbers of equivalents of reagents are all the numbers of equivalents to the compound represented by formula (A).

Examples of usable solvents include aromatic hydrocarbon-based solvents such as toluene, xylene, and ethylbenzene; ester-based solvents such as methyl acetate, ethyl acetate, and butyl acetate; ether-based solvents such as diethyl ether, diisopropyl ether, tetrahydrofuran, dioxane, dimethoxyethane, and tert-butyl methyl ether; aprotic polar organic solvents such as N,N-dimethylformamide, dimethyl sulfoxide, N,N-dimethylacetamide, N-methyl-2-pyrrolidinone, 1,3-dimethyl-2-imidazolidinone, and acetonitrile; halogen-containing solvents such as dichloromethane and chloroform; hydrocarbon-based solvents such as cyclohexane; ketone-based solvents such as acetone and methyl ethyl ketone; water; and mixture solvents thereof.

Examples of preferred solvents include toluene, ester-based solvents, ether-based solvents, and mixture solvents thereof.

Examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; organic bases such as 1,8-diazabicyclo[5.4.0]undec-7-ene, 1,5-diazabicyclo[4.3.0]non-5-ene, triethylamine, diisopropylethylamine, pyridine, picoline, dimethylaminopyridine, and N-methylimidazole; and alcoholates such as sodium ethoxide, sodium methoxide, and potassium tert-butoxide. The base does not necessarily need to be used; however, when the reaction is carried out in the presence of a base, examples of preferred bases include pyridine and N-methylimidazole. When the react ion is carried out in the presence of a base, the amount of the base used is 0.01 to 20.0 equivalents, preferably 1.0 to 5.0 equivalents.

The trifluoroacetic acid as an acylating agent can be used alone but, as needed, may be used in combination with one or at least two of other acylating agents such as trifluoroacetic anhydride, trifluoroacetyl chloride, and ethyl trifluoroacetate. Of these acylating agents, trifluoroacetic acid is preferably used alone. The amount of the acylating agent used is preferably 0.5 to 10.0 equivalents, and more preferably 1.0 to 5.0 equivalents.

Further, examples of the reagent (X) simultaneously used include at least one or more reagents selected from thionyl chloride, phosphorus oxychloride, oxalyl dichloride, and the like. These can be used alone or in combination. The reagent (X) is preferably used in an amount of 0.2 to 5.0 equivalents.

The reaction temperature is preferably in a range from −80° C. to 200° C. The reaction time is preferably in a range from 0.1 hours to 7 days.

More preferred conditions are as follows: toluene, an ether-based solvent, an ester-based solvent, or a mixture solvent thereof is used as the solvent; trifluoroacetic acid is used in an amount of 1.0 to 2.0 equivalents; one or more reagents selected from thionyl chloride, phosphorus oxychloride, and oxalyl dichloride are used in an amount of 0.3 to 3.0 equivalents; pyridine or N-methylimidazole is present as the base; the reaction temperature is −10° C. to 80° C.; and the reaction time is 0.1 hours to 1 day.

Particularly preferred conditions are the following conditions. Trifluoroacetic acid is used as the acylating agent; an ether-based solvent, an ester-based solvent, or a mixture solvent thereof is used as the solvent; and the amount of the acylating agent used is 1.0 to 2.0 equivalents. Further, thionyl chloride is simultaneously used in an amount of 0.5 to 1.5 equivalents. Furthermore, pyridine or N-methylimidazole is used as the base in an amount of 1.5 to 3.0 equivalents; the reaction temperature is −10° C. to 60° C.; and the reaction time is 0.1 hours to 12 hours.

[2] Production of Compound Represented by Formula (I) from Compound Represented by Formula (B)

A method for producing a compound represented by formula (I) from a compound represented by formula (B) is as follows. Specifically, the compound represented by formula (I) can be obtained by reacting the compound represented by formula (B) with a compound represented by formula (C) without a solvent or in a solvent in the presence of a base.

Examples of usable solvents include ether-based solvents such as diethyl ether, diisopropyl ether, tetrahydrofuran, dioxane, and tert-butyl methyl ether; aprotic polar organic solvents such as N,N-dimethylformamide, dimethyl sulfoxide, N,N-dimethylacetamide, acetonitrile, N-methyl-2-pyrrolidinone, N-methyl-2-piperazinone, N,N-dimethyl-2-imidazolidinone, and acetonitrile; ester-based solvents such as methyl acetate, ethyl acetate, and butyl acetate; halogen-containing solvents such as dichloromethane and chloroform; aromatic hydrocarbon-based solvents such as toluene, xylene, and ethylbenzene; and mixture solvents thereof; and preferred examples thereof include aprotic polar organic solvents. Here, more preferable is a mixture solvent of an aromatic hydrocarbon-based solvent with one or at least two solvents selected from the group consisting of N,N-dimethylformamide, dimethyl sulfoxide, N,N-dimethylacetamide, N-methyl-2-pyrrolidinone, N,N-dimethyl-2-imidazolidinone, and acetonitrile, or with one or at least two solvents selected from the group consisting of N, N-dimethylformamide, dimethyl sulfoxide, N,N-dimethylacetamide, N-methyl-2-pyrrolidinone, N,N-dimethyl-2-imidazolidinone, and acetonitrile; and particularly preferable is dimethyl sulfoxide alone, N,N-dimethylformamide alone, or a mixture solvent of dimethyl sulfoxide with toluene, or a mixture solvent of N,N-dimethylformamide with toluene.

When the reaction is carried out in the presence of a base, examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; and organic bases such as 1,8-diazabicyclo[5.4.0]undec-7-ene, 1,5-diazabicyclo[4.3.0]non-5-ene, triethylamine, diisopropylethylamine, pyridine, lutidine, collidine, N,N-dimethylaniline, and N,N-diethylaniline; preferred examples thereof include potassium carbonate, potassium hydrogen carbonate, pyridine, triethylamine, and the like; and more preferred examples thereof include potassium carbonate.

The amount of the compound represented by formula (C) used is preferably 0.7 to 2.0 equivalents, and more preferably 0.7 to 1.2 equivalents, to the compound represented by formula (B).

When the reaction is carried out in the presence of a base, the amount of the base used is preferably 1.0 to 10.0 equivalents, more preferably 1.0 to 6.0 equivalents, and particularly preferably 1.0 to 2.4 equivalents, to the compound represented by formula (B).

The reaction temperature is preferably in a range from 20° C. to 100° C., and more preferably in a range from 40° C. to 80° C. The reaction time is preferably in a range from 0.1 hours to 3 days, and more preferably in a range from 1 hour to 1 day.

Particularly preferred conditions are as follows: N,N-dimethylformamide alone, dimethyl sulfoxide alone, a mixture solvent of N, N-dimethylformamide with toluene, or a mixture solvent of dimethyl sulfoxide with toluene is used as the solvent; the amount of the compound represented by formula (C) used is 0.7 to 1.2 equivalents to the compound represented by formula (B); the reaction temperature is 40° C. to 80° C.; the reaction time is 1 hour to 2 days; and potassium carbonate is used as the base in an amount of 1.0 to 2.4 equivalents.

[3] One-Pot Production for Obtaining Compound Represented by Formula (I) from Compound Represented by Formula (A) Through Compound Represented by Formula (B)

When the compound represented by formula (I) is synthesized from the compound represented by formula (A), the compound represented by formula (I) can be obtained by conducting the subsequent step, without isolation of the compound represented by formula (B).

Specifically, the compound represented by formula (I) can be obtained by a reaction in which the reaction product represented by formula (B) is used as it is or after the excessive reagent is removed under reduced pressure, or after a by-produced salt of the organic base is removed by filtration, phase separation, or other operations; the compound represented by formula (C) and the base are added thereto; and a reaction therebetween is allowed to proceed under the above-described conditions.

A preferred example of the method for obtaining the compound represented by formula (I) from the compound represented by formula (A) through the compound represented by formula (B) is a method in which a compound represented by formula (A) is reacted with trifluoroacetic acid as an acylating agent by use of an ether-based solvent, an ester-based solvent, or a mixture solvent thereof, to thereby obtain a compound represented by formula (B); then a by-produced salt of the organic base is removed by filtration, phase separation, or other operations; a compound represented by formula (C), a base, and an aromatic hydrocarbon-based solvent, an aprotic polar organic solvent, or a mixture solvent thereof are added; and a reaction therebetween is allowed to proceed, as it is or while the aromatic hydrocarbon-based solvent is distilled off under reduced pressure, to thereby obtain a compound represented by formula (I).

[4] Production of Compound Represented by Formula (B) from Compound Represented by Formula (A) in One-Pot Production Here, the numbers of equivalents of reagents are all the numbers of equivalents to the compound represented by formula (A).

When trifluoroacetic acid is used as the acylating agent, particularly preferred conditions are as follows.

Trifluoroacetic acid is used as the acylating agent; an ether-based solvent, an ester-based solvent, or a mixture solvent thereof is used as the solvent; and the amount of the acylating agent used is 1.0 to 2.0 equivalents. Further, thionyl chloride is simultaneously used in an amount of 0.5 to 1.5 equivalents. Furthermore, pyridine or N-methylimidazole is used as the base in an amount of 1.5 to 3.0 equivalents; the reaction temperature is −10° C. to 60° C.; and the reaction time is 0.1 hours to 12 hours.

[5] Production of Compound Represented by Formula (I) from Compound Represented by Formula (B) in One-Pot Production Particularly preferred conditions for obtaining a compound represented by formula (I) from a compound represented by formula (B) are as follows: N,N-dimethylformamide alone, dimethyl sulfoxide alone, a mixture solvent of N,N-dimethyl formamide with toluene, or a mixture solvent of dimethyl sulfoxide with toluene is used as the solvent; the amount of the compound represented by formula (C) used is 0.7 to 1.2 equivalents to the compound represented by formula (B); the reaction temperature is 40° C. to 80° C.; the reaction time is 1 hour to 2 days; and potassium carbonate is used as the base in amount of 1.0 to 2.4 equivalents.

[6] Method for Purifying and Isolating Compound Represented by Formula (I) from Crude Product The compound represented by formula (I) can be purified and isolated by any one of or a combination of crystallization, solvent extraction, column chromatography, and the like, which are ordinarily employed. The solvent used for the solvent extraction is not particularly limited, as long as the solvent is immiscible with water, and specific examples thereof include ethyl acetate, butyl acetate, toluene, ethylbenzene, diethyl ether, diisopropyl ether, dichloromethane, chloroform, and the like. Examples of the solvent used for the crystallization include water, hexane, toluene, acetone, N,N-dimethylformamide, dimethyl sulfoxide, methanol, 2-propanol, dichloromethane, chloroform, ethyl acetate, diethyl ether, xylene, N-methyl-2-pyrrolidinone, N,N-dimethylacetamide, and the like; as well as mixture solvents of any of these.

A preferred method for purifying and isolating the compound represented by formula (I) is crystallization. Here, one of or a combination of acetone, toluene, water, N,N-dimethylformamide, dimethyl sulfoxide, methanol, xylene, N-methyl-2-pyrrolidinone, and N,N-dimethylacetamide is preferably used as a crystallization solvent, and combinations selected from water, methanol, N,N-dimethylformamide, and dimethyl sulfoxide are more preferable.

EXAMPLES

Specific examples of the present invention are shown below; however, the present invention is not limited thereto.

Synthesis Example 1

Synthesis of N-[1-((6-chloropyridin-3-yl)methyl) pyridin-2(1H)-ylide ne]-2,2,2-trifluoroacetamide In 34.7 g of 1,2-dimethoxyethane and 34.8 g of pyridine, 18.8 g of 2-aminopyridine was dissolved, and 25.1 g of trifluoroacetic acid and 26.2 g of thionyl chloride were added dropwise in this order at 0° C., followed by stirring at room temperature for 1 hour. The reaction liquid was concentrated under reduced pressure at 110 hPa and 50° C. for 25 minutes. Then, 26 g of 1,2-dimethoxyethane was added thereto. A solid precipitated was removed by filtration, and the solid was washed using a total of 86.8 g of 1,2-dimethoxyethane to add the washing liquid to the filtrate.

The filtrate was concentrated under reduced pressure. To the residue, 33.4 g of 2-chloro-5-chloromethylpyridine 55 g of dimethyl sulfoxide, 17.3 g of toluene, and 19.3 g of potassium carbonate (powder) were added and stirred at 60°

C. and 130 hPa for 2 hours and at 70° C. and 80 hPa for 1 hour. Then, the reaction liquid was poured into 120 g of water, and a solid remaining in the pear-shaped flask was washed using approximately 7.9 g of methanol to add the washing liquid to the mixture. After this mixture was stirred at room temperature for 1 hour, a solid precipitated was collected by filtration, washed by spraying twice with 40 g of water and twice with 34.7 g of toluene, and then dried under reduced pressure overnight. Thus, 56.5 g of the target compound was obtained (Percentage Yield 90%).

1H-NMR (CDCl3, δ, ppm):
5.57 (2H, s), 6.92 (1H, td), 7.31 (1H, d), 7.80 (1H, td), 7.87 (1H, dd), 7.99 (1H, dd), 8.48 (2H, m)
13C-NMR (CDCl3,δ, ppm): 53.8, 115.5, 117.2 (q), 122.1, 124.7, 130.0, 139.2, 140.0, 142.5, 149.7, 151.8, 158.9, 163.5 (q)
MS: m/z=316 (M+H).

Synthesis Example 2

Synthesis of N-[1-((6-chloropyridin-3-yl)methyl)pyridin-2(1H)-ylide ne]-2,2,2-trifluoroacetamide In 26 g of toluene and 9.5 g of pyridine, 4.7 g of 2-aminopyridine was dissolved, and 6.27 g of trifluoroacetic acid and 6.54 g of thionyl chloride were added dropwise in this order at 0° C., followed by stirring at room temperature for 1 hour. The reaction liquid was concentrated under reduced pressure at 120 hPa and 60° C. for 10 minutes. Then, 17.3 g of toluene was added thereto, and concentrated under reduced pressure at 110 hPa and 60° C. for 10 minutes. A solid precipitated was removed by filtration, and the solid was washed using a total of 39 g of toluene.

To the filtrate, 8.05 g of 2-chloro-5-chloromethylpyridine, 70.8 g of N,N-dimethylformamide, and 8.28 g of potassium carbonate (powder) were added and stirred at 60° C. and 130 hPa for 2 hours and at 70° C. and 80 hPa for 1 hour. Then, the reaction liquid was poured into 80 g of water, and a solid remaining in the pear-shaped flask was washed with a total of 7.9 g of methanol to add the washing liquid to the mixture. After this mixture was stirred at room temperature for 1 hour, a solid precipitated was collected by filtration, washed by spraying twice with 20 g of water and twice with 17.3 g of toluene, and then dried under reduced pressure overnight. Thus, 13.02 g of the target compound was obtained (Percentage Yield 83%).

Synthesis Example 3

Synthesis of N-[1-((6-chloropyridin-3-yl)methyl)pyridin-2(1H)-ylide ne]-2,2,2-trifluoroacetamide In 56.4 g of dioxane, 28.2 g of 2-aminopyridine was dissolved, and 54.2 g of N-methylimidazole was added to this solution. Under ice-cooling, 35.9 g of trifluoroacetic acid and 41.0 g of thionyl chloride were added thereto. After stirring at room temperature for 1.5 hours, the dioxane layer was separated, and the lower layer was extracted with 56.4 g of dioxane. The extraction was repeated three times, and the collected dioxane layer was concentrated. To the residue, 46.2 g of 2-chloro-5-chloromethylpyridine, 66.6 g of N,N-dimethylformamide, 24.4 g of toluene, and 29.0 g of potassium carbonate were added, and the reaction was allowed to proceed at 60° C. under reduced pressure of 120 to 80 hPa for 4 hours. The reaction liquid was added dropwise to 170 g of hot water, and precipitates were filtered. The filtered material was washed with 84 g of water and 72.8 g of toluene, and then dried under reduced pressure. Thus, 82.6 g of the target compound was obtained (Percentage Yield 87.2%).

Synthesis Example 4

Synthesis of N-[1-((6-chloropyridin-3-yl)methyl)pyridin-2(1H)-ylide ne]-2,2,2-trifluoroacetamide In 35.6 g of tetrahydrofuran and 34.8 g of pyridine, 18.8 g of 2-aminopyridine was dissolved, and 25.1 g of trifluoroacetic acid and 26.2 g of thionyl chloride were added dropwise in this order at 0° C., followed by stirring at 40° C. for 1 hour. The tetrahydrofuran layer was separated, and extraction was conducted twice using 35.6 g of tetrahydrofuran from the lower layer, while warming to 45° C. All the extraction liquids were combined and concentrated under reduced pressure. To the residue, 32.2 g of 2-chloro-5-chloromethylpyridine dissolved in 55 g of dimethyl sulfoxide, 17.3 g of toluene, and 19.3 g of potassium carbonate (powder) were added in this order, and stirred at 60° C. and 130 hPa for 2 hours and at 70° C. and 80 hPa for 1 hour. Then, the reaction liquid was poured into 120 g of water. After this mixture was stirred at room temperature for 1 hour, a solid precipitated was collected by filtration, washed by spraying twice with 40 g of water and twice with 34.7 g of toluene, and then dried under reduced pressure overnight. Thus, 55.3 g of the target compound was obtained (Percentage Yield 88%).

Synthesis Example 5

Synthesis of N-[1-((6-chloropyridin-3-yl)methyl)pyridin-2(1H)-ylide ne]-2,2,2-trifluoroacetamide In a mixture solvent of 34.8 g of pyridine and 37.6 g of tert-butyl methyl ether, 18.8 g of 2-aminopyridine was dissolved, and 23.9 g of trifluoroacetic acid and 26.2 g of thionyl chloride were added under ice-cooling, followed by stirring at room temperature for 1 hour. The reaction liquid was filtered, followed by washing three times with 18.7 g of tert-butyl methyl ether. All the filtrates were combined, and the solvent was distilled off under reduced pressure. The resultant was dissolved in 51.7 g of dimethyl sulfoxide and 16.2 g of 2-chloro-5-chloromethylpyridine added thereto. Further, 19.3 g of potassium carbonate powder was added and stirred at 60° C. for 2 hours and 70° C. for 30 minutes. The reaction liquid was added to 120 g of water. After being cooled to room temperature, the mixture was stirred for 30 minutes. The crystals were filtered, and washed four times with 40 g of water and twice with 34.7 g of toluene. The obtained crystals were dried under reduced pressure at 60° C. Thus, 53.4 g of the target compound was obtained (Percentage Yield 84.8.%).

Synthesis Example 6

Synthesis of N-[1-((6-chloropyridin-3-yl)methyl)pyridin-2(1H)-ylide ne]-2,2,2-trifluoroacetamide In 37.6 g of dioxane, 18.8 g of 2-aminopyridine was dissolved, and 34.8 g of pyridine was added to this solution. Under ice-cooling, 23.9 g of trifluoroacetic acid and 26.2 g of thionyl chloride were added thereto. After stirring at room temperature for 45 minutes, the dioxane layer was separated, and the lower layer was extracted with 37.6 g of dioxane. The extraction was repeated three times, and the collected dioxane layer was concentrated under reduced pressure. To the residue, 32.4 g of 2-chloro-5-chloromethylpyridine, 73.7 g of dimethyl sulfoxide, 40.7 g of toluene, and 19.3 g of potassium carbonate were added and stirred at 60° C. under reduced pressure of 100 hPa for 2 hours. Further, 2.76 g of potassium carbonate was added thereto and stirred under the same conditions for 1 hour. The reaction liquid was added dropwise to 180 g of hot water, followed by washing with 7.9 g of methanol to add the washing liquid to the mixture. After stirring at room temperature for 1 hour, precipitates were filtered. The filtered material was washed with water and toluene, and then temporarily dried under reduced pressure. The resultant was washed again with water, and then dried again under reduced pressure. Thus, 58.6 g of the target compound was obtained (Percentage Yield 93.0%).

Synthesis Example 7

Recovery of Pyridine

For example, from the pyridine hydrochloride obtained according to Synthesis Example 6, dioxane was distilled off under reduced pressure. Thus, 185 g of crude pyridine hydrochloride was obtained. The crude pyridine hydrochloride was neutralized by adding a 7 N ammonia solution in methanol under ice-cooling. Then, distillation was conducted. The distillate of approximately 110 to 114° C. was recovered. Thus, 93.3 g of pyridine was obtained.

Synthesis Example 8

Recovery of Pyridine

For example, from the pyridine hydrochloride obtained according to Synthesis Example 6, dioxane was distilled off under reduced pressure. Thus, 282 g of crude pyridine hydrochloride was obtained. After dissolved in 100 g of methanol added, the crude pyridine hydrochloride was neutralized by adding 118.8 g of sodium methoxide under ice-cooling. Then, 87 g of liquid paraffin was added thereto. Distillation was conducted, and the distillate of approximately 110 to 114° C. was recovered. Thus, 116.4 g of pyridine was obtained.

Synthesis Example 9

Recovery of Pyridine

For example, from the pyridine hydrochloride obtained according to Synthesis Example 6, dioxane was distilled off under reduced pressure. Thus, 136.1 g of crude pyridine hydrochloride was obtained. The crude pyridine hydrochloride was neutralized by adding 32 g of water and 100 g of 48% caustic soda, and extracted with 90 g of ethyl acetate. To the water phase, 120 g of water was added, and the extraction was conducted again with 45 g of ethyl acetate. The ethyl acetate layers were combined and distilled off. After the distillate of approximately 76° C. was removed, 20 g of cyclohexane was added to the residue, and water was removed by a dean-stark trap. After cyclohexane was removed by distillation, the residue was distilled off, and the distillate of approximately 114° C. was recovered. Thus, 57.8 g of pyridine was obtained.

Synthesis Example 10

Synthesis of N-[1-((6-chloropyridin-3-yl)methyl) pyridin-2(1H)-ylide ne]-2,2,2-trifluoroacetamide In 35.5 g of dioxane, 18.8 g of 2-aminopyridine was dissolved, and 30.1 g of the pyridine recovered in Synthesis Example 8 and 7 g of fresh pyridine were added to this solution. Under ice-cooling, 23.9 g of trifluoroacetic acid and 26.2 g of thionyl chloride were added thereto. After stirring at room temperature for 45 minutes, the dioxane layer was separated, and the lower layer was extracted with 37.6 g of dioxane. The extraction was repeated twice, and the collected dioxane layer was concentrated. To the residue, 30.8 g of 2-chloro-5-chloromethylpyridine, 51.7 g of dimethyl sulfoxide, and 19.3 g of potassium carbonate were added and stirred at 60° C. for 3 hours and at 70° C. for 1 hour. The reaction liquid was added dropwise to 110 g of water, and the reaction vessel was washed with 7.9 g of methanol to add the washing liquid to the mixture. After stirring at room temperature for 1 hour, precipitates were filtered. The filtered material was washed with water and toluene, and then dried under reduced pressure. Thus, 53.2 g of the target compound was obtained (Percentage Yield 84.3%).

Synthesis Example 11

Synthesis of N-[1-((6-chloropyridin-3-yl)methyl) pyridin-2(1H)-ylide ne]-2,2,2-trifluoroacetamide In 37.6 g of ethyl acetate and 34.8 g of pyridine, 18.8 g of 2-aminopyridine was dissolved. Under ice-cooling, 23.9 g of trifluoroacetic acid and 26.2 g of thionyl chloride were added thereto. After stirring at 45° C. for 45 minutes, the ethyl acetate layer was separated, and the lower layer was extracted with 37.6 g of ethyl acetate at 45° C. The extraction was repeated twice, and the collected ethyl acetate layer was concentrated. To the residue, 32.4 g of 2-chloro-5-chloromethylpyridine, 62 g of dimethyl sulfoxide, and 19.3 g of potassium carbonate were added and stirred at 60° C. for 3 hours. The reaction liquid was added dropwise to 132 g of water, and the reaction vessel was washed with 9.5 g of methanol to add the washing liquid to the mixture. After stirring at room temperature for 1 hour, precipitates were filtered. The filtered material was washed with 200 g of water and 100 g of toluene, and then dried under reduced pressure. Thus, 57.8 g of the target compound was obtained (Percentage Yield 91.7%).

Synthesis Example 12

Synthesis of N-[1-((6-chloropyridin-3-yl)methyl) pyridin-2(1H)-ylide ne]-2,2,2-trifluoroacetamide In 18.8 g of butyl acetate and 17.4 g of pyridine, 9.4 g of 2-aminopyridine was dissolved. Under ice-cooling, 11.97 g of trifluoroacetic acid and 13.1 g of thionyl chloride were added thereto. After stirring at 45° C. for 30 minutes, the butyl acetate layer was separated, and the lower layer was extracted with 18.8 g of butyl acetate at 45° C. The extraction was repeated twice, and the collected butyl acetate layer was concentrated. To the residue, 16.0 g of 2-chloro-5-chloromethylpyridine, 31 g of dimethyl sulfoxide, and 9.7 g of potassium carbonate were added and stirred at 60° C. under reduced pressure of 80 hPa for 2 hours. The reaction liquid was added dropwise to 75 g of water, and the reaction vessel was washed with 6 g of methanol to add the washing liquid to the mixture. After stirring at room temperature for 1 hour, precipitates were filtered. The filtered material was washed with 100 g of water and 52.2 g of toluene, and then dried under reduced pressure. Thus, 28.8 g of the target compound was obtained (Percentage Yield 91.4%).

Synthesis Example 13

Synthesis of N-[1-((6-chloropyridin-3-yl)methyl) pyridin-2(1H)-ylide ne]-2,2,2-trifluoroacetamide In 188 g of ethyl acetate and 174 g of pyridine, 94 g of 2-aminopyridine was dissolved. At temperatures of 6 to 30° C., 119.7 g of trifluoroacetic acid and 131 g of thionyl chloride were added thereto. After stirring at 35 to 45° C. for 30 minutes, 94 g of ethyl acetate was added thereto and stirred again at 30° C. for 45 minutes. The mixture was filtered, and 188 g of ethyl acetate was added to the reaction vessel. The remaining residue was stirred at 30° C. for 5 minutes and washed. The resultant was filtered again, and 94 g of ethyl acetate was added to the reaction vessel again. The remaining residue was stirred at 30° C. for 5 minutes and washed. The resultant was filtered again, and all the filtrates were combined. Then, the solvent was concentrated. To the residue, 156.3 g of 2-chloro-5-chloromethylpyridine, 310 g of dimethyl sulfoxide, and 96.6 g of potassium carbonate were added and stirred at 60° C. under reduced pressure of 300 hPa for 2.5 hours. The reaction liquid was added dropwise to 670 g of water, and the reaction vessel was washed with 79 g of methanol to add the washing liquid to the mixture. After stirring at room temperature for 1 hour, precipitates were filtered. The filtered material was washed with 1000 g of water and 433 g of toluene, and then dried under reduced pressure. Thus, 275 g of the target compound was obtained (Percentage Yield 87.1%).

Synthesis Example 14

Synthesis of N-[1-((6-chloropyridin-3-yl)methyl) pyridin-2(1H)-ylide ne]-2,2,2-trifluoroacetamide In 282 g of ethyl acetate and 174 g of pyridine, 94 g of 2-aminopyridine was dissolved. At temperatures of 6 to 30° C., 119.7 g of trifluoroacetic acid and 131 g of thionyl chloride were added thereto. After stirring at 35 to 45° C. for 30 minutes, the mixture was stirred again at 30° C. for 90 minutes. The mixture was filtered, and 188 g of ethyl acetate was added to the reaction vessel. The remaining residue was stirred at 30° C. for 5 minutes and washed. The resultant was filtered again, and 188 g of ethyl acetate was added thereto. The remaining residue was stirred at 30° C. for 5 minutes and washed. The resultant was filtered again, and 94 g of ethyl acetate was added to the reaction vessel again. The remaining residue was stirred at 30° C. for 5 minutes and washed. The resultant was filtered again, and all the filtrates were combined. Then, the solvent was concentrated. To the residue, 150.3 g of 2-chloro-5-chloromethylpyridine, 267 g of dimethyl sulfoxide, and 96.6 g of potassium carbonate were added and stirred at 60° C. under reduced pressure of 150 hPa for 2 hours. After the temperature was raised to 70° C., the reaction liquid was added dropwise to 564 g of water, and the reaction vessel was washed with 94 g of water and 55 mL of methanol to add the washing liquids to the mixture. After stirring at room temperature for 2 hours, precipitates were filtered. The filtered material was washed with 600 mL of water and 400 mL of 60% methanol, and then dried under reduced pressure. Thus, 269.3 g of the target compound was obtained (Percentage Yield 85.5%).

Synthesis Example 15

Synthesis of N-[1-((6-chloropyridin-3-yl)methyl) pyridin-2(1H)-ylide ne]-2,2,2-trifluoroacetamide In 28.2 g of ethyl acetate and 11.9 g of pyridine, 4.7 g of 2-aminopyridine was dissolved. At temperatures of 0 to 40° C., 11.4 g of trifluoroacetic acid and 8.9 g of thionyl chloride were added thereto. After stirring at 35 to 45° C. for 30 minutes, the ethyl acetate layer was collected, and the lower layer was extracted with 14.1 g of ethyl acetate. The extraction was repeated twice, and the collected ethyl acetate layer was concentrated. To the residue, 8.76 g of 2-chloro-5-chloromethylpyridine, 17 g of dimethyl sulfoxide, and 8.28 g of potassium carbonate were added and stirred at 60° C. for 4 hours. After the temperature was raised to 70° C., the reaction liquid was added dropwise to 50 g of water, and the reaction vessel was washed with 5 mL of methanol to add the washing liquid to the mixture. After stirring at room temperature for 1 hour, precipitates were filtered. The filtered material was washed with 20 mL of water and 20 mL of 60% methanol, and then dried under reduced pressure. Thus, 14.7 g of the target compound was obtained (Percentage Yield 93.1%).

INDUSTRIAL APPLICABILITY

As described above, according to the present invention, it is possible to produce a 2-acyliminopyridine derivative represented by formula (I), which is useful as a pest control agent, industrially advantageously with low environmental load and, if necessary, in a one-pot manner, and in turn to provide the 2-acyliminopyridine derivative in an amount required as a pest control agent stably and at a low cost. Accordingly, the present invention greatly contributes to the field of pest control.

The invention claimed is:

1. A method for producing a compound represented by the following formula (I):

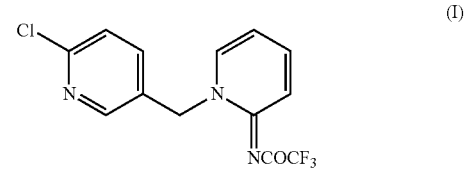

the production method comprising, as shown in the following reaction formula:

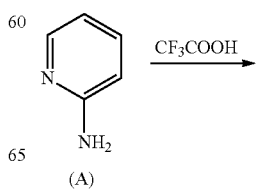

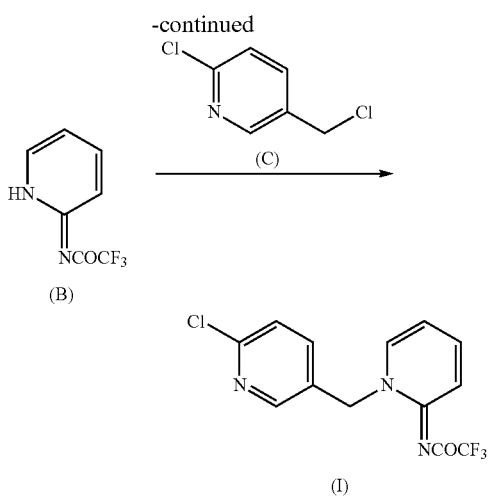

the steps of:
acylating an amino group at position 2 of a compound represented by formula (A) in the presence of trifluoroacetic acid as an acylating agent, a reagent (X) (where the reagent (X) is at least one reagent selected from thionyl chloride, phosphorus oxychloride, and oxalyl dichloride), and a base, to thereby produce a compound represented by formula (B); and
further alkylating a nitrogen atom at position 1 of the compound represented by formula (B) by use of a compound represented by formula (C).

2. The production method according to claim 1, wherein the reagent (X) used simultaneously with the acylating agent is thionyl chloride.

3. The production method according to claim 1, wherein the base used in the reaction of the compound represented by formula (B) is pyridine or N-methylimidazole.

4. The production method according to claim 1, wherein a solvent used in the reaction of the compound represented by formula (B) is an ether-based or ester-based solvent.

* * * * *